United States Patent [19]

Shipchandler

[11] 4,092,326
[45] May 30, 1978

[54] PROCESS FOR PRODUCTION OF SUBSTITUTED OXAZOLINES

[75] Inventor: Mohammed T. Shipchandler, Terre Haute, Ind.

[73] Assignee: IMC Chemical Group, Inc., Terre Haute, Ind.

[21] Appl. No.: 749,859

[22] Filed: Dec. 13, 1976

[51] Int. Cl.$^2$ .......................................... C07D 263/14
[52] U.S. Cl. .................................................. 260/307 F
[58] Field of Search ....................... 260/307 F, 307 FA

[56] References Cited

U.S. PATENT DOCUMENTS 3,074,956  1/1963  Meyer ................................... 260/307

Primary Examiner—Raymond V. Rush

Attorney, Agent, or Firm—Robert H. Dewey; Howard E. Post

[57] ABSTRACT

A method for the production of 2-[(2-hydroxymethyl)-phenyl]-2-oxazolines by condensing o-phthalaldehyde with an alkanolamine represented by the formula

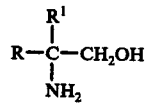

where R is an alkyl group of 1 to 3 carbon atoms and $R^1$ is hydrogen or methyl. The compounds have utility as tranquilizing agents.

6 Claims, No Drawings

PROCESS FOR PRODUCTION OF SUBSTITUTED OXAZOLINES

BACKGROUND OF THE INVENTION

This invention relates to a process for the production of substituted oxazolines. In a particular aspect, this invention relates to a process for the production of 2-[(2-hydroxymethyl)phenyl]-2-oxazolines.

Oxazolines have a wide variety of uses. Many of them are oil-soluble surface-active agents, anti-corrosion agents, and monomers for coatings. Also many have pharmaceutical applications. Thus L. F. Wiggins et al. in U.S. Pat. No. 3,235,557, which is incorporated herein by reference, and H. L. Wehrmeister, U.S. Pat. No. 3,953,432, disclosed oxazolines having tranquilizing activity.

The conventional method of preparing oxazolines is to condense an alkanolamine with a carboxylic acid at elevated temperatures as disclosed by Purcell, U.S. Pat. No. 3,336,145. However, due to side reactions, the oxazoline was obtained in only moderate yield and was difficult to purify. Accordingly there is a need for another process of making oxazolines, especially those intended for pharmaceutical application.

SUMMARY OF THE INVENTION

It is an object of this invention to provide a method for the production of certain substituted oxazolines.

It is another object of this invention to provide a method for the production of 2-[(2-hydroxymethyl)phenyl]-2-oxazolines.

Other objects will be apparent to those skilled in the art from the description herein.

It is the discovery of this invention to condense o-phthalaldehyde with a β-alkanolamine represented by the formula

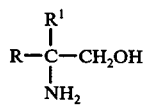

where R is an alkyl group of 1 to 3 carbon atoms, $R^1$ is hydrogen or methyl, thereby producing an oxazoline represented by the formula

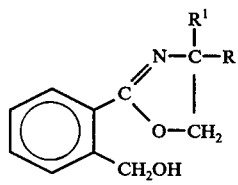

where R and $R^1$ have the same meanings defined above. These compounds have utility as tranquilizers in animals. Analogs of these compounds, where R and $R^1$ are hydroxymethyl, are known from Wiggins et al., cited above.

DETAILED DISCUSSION

The reaction which forms the basis for the process of this invention occurs readily at ambient temperatures with the evolution of heat. The reaction is nearly quantitative. o-Phthalaldehyde is a known compound, available commercially. The usual commercial quality is suitable for the practice of this invention.

The alkanolamines used in the practice of this invention are known compounds and include 2-amino-1-propanol, 2-amino-1-butanol and 2-amino-2-methyl-1-propanol.

According to the process of this invention, the dialdehyde and β-alkanolamine are mixed in a mole ratio of about 1:1 in the presence of a suitable solvent, e.g. a lower aliphatic alcohol, benzene, toluene or xylene. The reaction proceeds rapidly at room temperature, typically with a 10°–20° rise in temperature, depending on the volume of solvent.

The product can be conveniently recovered by evaporating the solvent. If preferred, the oxazoline can be further purified by distillation.

It is very surprising that o-phthalaldehyde would react with a β-amino alcohol to form an oxazoline, since it is known from M. Senkus, J. Am. Chem. Soc. 67, 1515 (1945) and others that the reaction of an aldehyde with an alkanolamine yields an oxazolidine.

The oxazolines of this invention have utility as tranquilizers for animals in need of tranquilizing when tested either by the method described by Wiggins or by those described by Wehrmeister, references cited hereinbefore. In general these compounds, which are of a low order of toxicity, are effective at a dosage between 100 and 1000 mg/kg of body weight.

The invention will be better understood with reference to the following examples. It is understood, however, that the examples are intended only to illustrate the invention and it is not intended that the invention be limited thereby.

EXAMPLE 1 o-Phthalaldehyde 13.4 g (0.1 mole) was dissolved in 20 ml of benzene and then was mixed with 2-amino-2-methyl-propanol 8.9 g (0.1 mole) dissolved in 10 ml benzene. The heat of reaction elevated the temperature to the boiling point of the solvent. The reaction mixture was stirred for 2 hours without temperature control. Water of reaction was removed by coevaporation with 20 ml portions of benzene. About 20 g of yellow oil was obtained. It was distilled at 165° and 0.5 mm which gave an oil which crystallized from benzene-cyclohexane, m.p. 78°–79°. The infrared spectrum and analysis were consistent with 4,4-dimethyl-2-[(2-hydroxymethyl)-phenyl]-2-oxazoline.

This compound has tranquilizing activity when administered to animals at a dosage of 100 to 1000 mg/kg of body weight.

EXAMPLE 2

The experiment of Example 1 was repeated in all essential details except that 2-amino-1-butanol was substituted for 2-amino-2-methylpropanol. A brown oil was obtained. It was characterized by gas chromotography and high resolution mass spectrometry. The data obtained were consistent with the proposed structure 4-ethyl-2-[(2-hydroxy-methyl)phenyl]-2-oxazoline.

This compound shows tranquilizing activity when administered to animals at a dosage of 100 to 1000 mg/kg of body weight.

EXAMPLE 3

The experiment of Example 1 was repeated in all essential details except that 2-amino-3-methyl-1-butanol was substituted for 2-amino-2-methylpropanol. There was obtained 4-(1-methylethyl)-2-[2-(hydroxymethyl)-phenyl]-2-oxazoline, m.p. 62°-72°. It was characterized by its infrared absorption spectrum, proton magnetic resonance spectrum and carbon, hydrogen and nitrogen analysis.

This compound has tranquilizing activity when administered to animals at a dosage of 100 to 1000 mg/kg of body weight.

I claim:

1. A method for the production of oxazolines represented by the formula

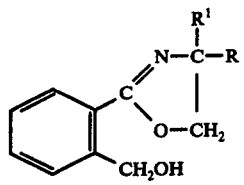

where r is an alkyl group of 1 to 3 carbon atoms and $R^1$ is hydrogen or methyl comprising reacting an alkanolamine represented by the formula

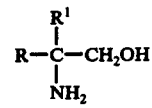

with o-phthalaldehyde in a 1:1 mole ratio at room temperature.

2. The method of claim 1 wherein $R^1$ is hydrogen.
3. The method of claim 1 wherein $R^1$ is methyl.
4. The method of claim 1 wherein R is methyl.
5. The method of claim 1 wherein R is ethyl.
6. The method of claim 2 wherein R is isopropyl.

* * * * *

UNITED STATES PATENT AND TRADEMARK OFFICE
CERTIFICATE OF CORRECTION

PATENT NO. : 4,092,326

DATED : May 30, 1978

INVENTOR(S) : Mohammed T. Shipchandler

It is certified that error appears in the above–identified patent and that said Letters Patent are hereby corrected as shown below:

Column 4, line 10, "r" should read - R -

Signed and Sealed this

Thirty-first Day of October 1978

[SEAL]

Attest:

RUTH C. MASON
*Attesting Officer*

DONALD W. BANNER
*Commissioner of Patents and Trademarks*